United States Patent
Misle et al.

(10) Patent No.: US 10,507,072 B1
(45) Date of Patent: Dec. 17, 2019

(54) STERILE STAND FOR SUPPORTING SURGICAL INSTRUMENTS

(71) Applicants: Gayle Misle, Millbrae, CA (US); Ryan C. Patterson, Farmington, UT (US); Trent J. Perry, Kaysville, UT (US)

(72) Inventors: Gayle Misle, Millbrae, CA (US); Ryan C. Patterson, Farmington, UT (US); Trent J. Perry, Kaysville, UT (US)

(73) Assignee: Gayle Misle, Millbrae, CA (US)

( * ) Notice: Subject to any disclaimer, the term of this patent is extended or adjusted under 35 U.S.C. 154(b) by 2 days.

(21) Appl. No.: 15/898,857

(22) Filed: Feb. 19, 2018

(51) Int. Cl.
| | |
|---|---|
| *A61B 50/24* | (2016.01) |
| *A61B 50/22* | (2016.01) |
| *A61B 50/30* | (2016.01) |
| *A47F 7/00* | (2006.01) |

(52) U.S. Cl.
CPC ............ *A61B 50/24* (2016.02); *A47F 7/0028* (2013.01); *A61B 50/22* (2016.02); *A61B 50/3001* (2016.02)

(58) Field of Classification Search
CPC ......... A61B 90/50; A61B 50/22; A61B 50/24; A61B 50/3001; A47F 7/0021; A47F 7/0028
USPC ...... 211/85.13, 69.1, 69.5, 70; 206/214, 1.7, 206/366, 365
See application file for complete search history.

(56) References Cited

U.S. PATENT DOCUMENTS

| | | | | |
|---|---|---|---|---|
| 2,435,994 A * | 2/1948 | Zukerman | ............. | A61M 5/001 206/366 |
| 2,511,537 A * | 6/1950 | Migdow | ................. | B44D 3/02 206/1.7 |
| 2,557,222 A * | 6/1951 | Goode | ................. | A61M 5/001 206/365 |
| 2,557,420 A * | 6/1951 | Elliott | ........................ | A61L 2/26 206/210 |
| 2,740,516 A * | 4/1956 | Renn | ..................... | A61M 5/003 206/229 |
| 3,491,894 A * | 1/1970 | Brown | ..................... | B65D 1/36 211/74 |
| 3,866,992 A * | 2/1975 | Katz | .................... | B43M 99/007 211/69.5 |
| 4,142,633 A * | 3/1979 | Raghavachari | ....... | A61M 5/008 141/27 |
| 4,341,300 A * | 7/1982 | Roy | ..................... | B43M 99/002 206/523 |
| 4,850,484 A * | 7/1989 | Denman | ............... | A61M 5/008 206/366 |

(Continued)

FOREIGN PATENT DOCUMENTS

| | | | | |
|---|---|---|---|---|
| EP | 0053206 A1 * | 6/1982 | ............. | A61B 10/00 |
| EP | 3042626 A1 * | 7/2016 | ............... | A61C 3/04 |

(Continued)

*Primary Examiner* — Michael Safavi
(74) *Attorney, Agent, or Firm* — Dennis L. Thomte; Thomte Patent Law Office LLC

(57) ABSTRACT

A sterile stand for supporting surgical instruments or medical tools such as needles, cannulas, syringes and an injection needle assembly. The stand includes a base member having one or more support tubes extending upwardly therefrom. The support tube is configured to receive a portion of the surgical instrument extending downwardly thereinto. The base member also has a receptacle positioned thereon for receiving an injection needle assembly therein. The base member is configured to receive the lower end of one or more syringes.

5 Claims, 7 Drawing Sheets

(56) References Cited

U.S. PATENT DOCUMENTS

| | | | | |
|---|---|---|---|---|
| 4,863,023 A * | 9/1989 | Payne | B65D 43/0212 | 206/364 |
| 4,944,730 A * | 7/1990 | Plucinski | A61M 5/008 | 206/366 |
| 5,033,629 A * | 7/1991 | Caine | A47F 7/00 | 211/69.5 |
| 5,163,549 A * | 11/1992 | Hayduchok | A45C 11/34 | 206/214 |
| 5,232,103 A * | 8/1993 | Koenig | B43K 23/002 | 211/60.1 |
| 5,265,724 A * | 11/1993 | Dondlinger | A61M 5/3205 | 206/365 |
| 5,330,899 A * | 7/1994 | DeVaughn | B01L 3/5085 | 206/363 |
| 5,372,252 A * | 12/1994 | Alexander | A61M 5/001 | 206/210 |
| 5,396,989 A * | 3/1995 | Hein | A61B 17/205 | 206/366 |
| 5,435,979 A * | 7/1995 | Miller | A61C 3/04 | 206/369 |
| 5,447,243 A * | 9/1995 | Graber | B43M 99/008 | 206/371 |
| 5,462,163 A * | 10/1995 | Berry | A61M 5/002 | 206/370 |
| 5,533,618 A * | 7/1996 | Pickels, Jr. | A61B 50/20 | 206/363 |
| 5,544,764 A * | 8/1996 | Cima | B43M 99/008 | 211/60.1 |
| 5,850,917 A * | 12/1998 | Denton | A61M 5/008 | 206/366 |
| 6,279,743 B1 * | 8/2001 | Ballard | A61M 5/3213 | 128/852 |
| 6,382,575 B1 * | 5/2002 | Frush | A61L 2/26 | 211/85.13 |
| 7,314,142 B2 * | 1/2008 | Lyman, Jr. | B43K 23/002 | 206/214 |
| 7,611,012 B2 * | 11/2009 | Ross | A61M 5/008 | 206/366 |
| 8,069,998 B2 * | 12/2011 | Thomas | A61L 2/26 | 211/85.13 |
| 8,100,263 B2 * | 1/2012 | Vanderbush | A61M 5/002 | 206/366 |
| 8,267,246 B2 * | 9/2012 | Bettenhausen | A61B 50/34 | 206/363 |
| 8,485,357 B2 * | 7/2013 | Song | A61M 5/002 | 206/366 |
| 8,827,088 B1 * | 9/2014 | Krause | A61L 9/00 | 211/85.13 |
| 8,852,158 B1 * | 10/2014 | Schaffer | A61M 5/008 | 206/364 |
| 2002/0014560 A1 * | 2/2002 | Diamond | A61M 5/008 | 248/37.3 |
| 2007/0134142 A1 * | 6/2007 | Riley | A61L 2/26 | 422/300 |
| 2011/0017621 A1 * | 1/2011 | Zoland | A61B 50/13 | 206/363 |
| 2012/0080341 A1 * | 4/2012 | Finke | A61M 5/008 | 206/366 |
| 2012/0085720 A1 * | 4/2012 | Bettenhausen | A61L 2/26 | 211/85.13 |
| 2014/0021079 A1 * | 1/2014 | Koller | A47F 7/0028 | 206/370 |
| 2014/0197120 A1 * | 7/2014 | Seiwell | A61M 5/008 | 211/85.8 |
| 2014/0202903 A1 * | 7/2014 | Dassonville | A61C 3/04 | 206/370 |
| 2017/0035522 A1 * | 2/2017 | Roland | A61B 50/22 | |

FOREIGN PATENT DOCUMENTS

| | | | | |
|---|---|---|---|---|
| JP | 03158170 A * | 7/1991 | | A61J 1/2096 |
| WO | WO-9740869 A1 * | 11/1997 | | A61M 5/3205 |
| WO | WO-2014109011 A1 * | 7/2014 | | B65D 77/2024 |
| WO | WO-2014115256 A1 * | 7/2014 | | G09F 23/00 |

* cited by examiner

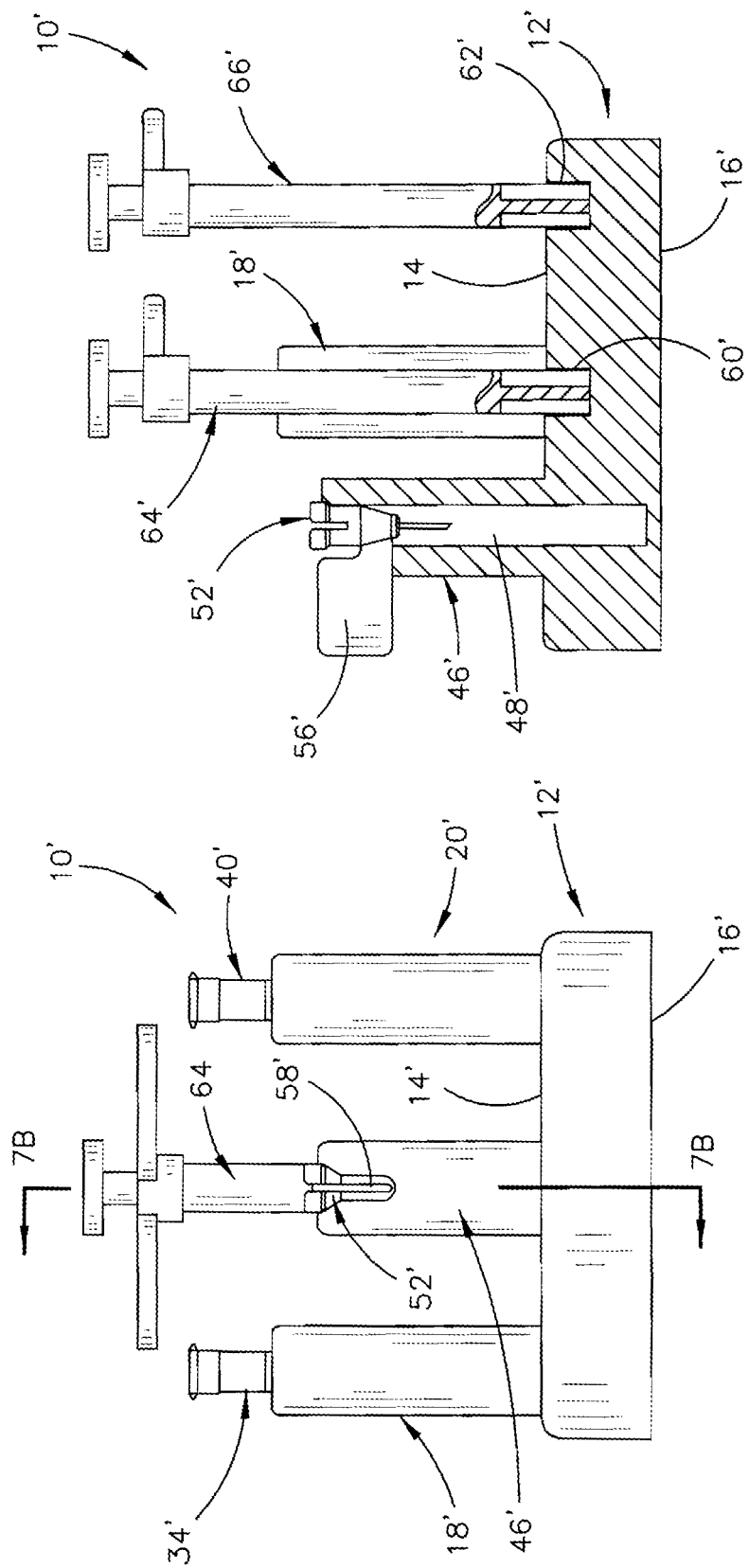

STERILE STAND FOR SUPPORTING SURGICAL INSTRUMENTS

BACKGROUND OF THE INVENTION

Field of the Invention

This invention relates to a sterile stand for supporting surgical instruments or medical tools such as epidural needles, blunt cannulas, syringes and an injection needle assembly.

Description of the Related Art

Applicants have previously filed U.S. patent application Ser. No. 15/133,660 filed Apr. 20, 2016 entitled CANNULA AND NEEDLE ASSEMBLY and U.S. patent application Ser. No. 15/354,249 filed Nov. 17, 2016 entitled EPIDURAL NEEDLE ASSEMBLY. In U.S. patent application Ser. No. 15/354,249, during the use of components thereof, there are occasions when the epidural needle or cannula needs to be removed from the patient to add additional local anesthetic or fillers to a syringe connected to the epidural needle or cannula. It is important during this procedure to maintain the epidural needle or cannula in a sterile condition if it is to be used again. Prior to the instant invention, maintaining the needle in a sterile condition required a two-handed technique. In the prior art procedure, one hand holds the syringe with the other hand removes the needle cap from the syringe. Then, the person must put the syringe down with one hand while the other hand grasps the needle cap and places it on the needle to keep it sterile.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

A stand is provided for supporting surgical instruments or medical tools such as needles, blunt cannulas, an injection needle assembly and syringes. The stand includes a horizontally disposed base member having a lower side and an upper side. A plurality of vertically disposed hollow sterile support tubes, having a lower end and an upper end, extend upwardly from the base member. The upper ends of the support tubes have an opening formed therein which has a diameter which is less than the diameter of the support tubes. Each of the support tubes is configured to have an elongated needle or cannula extending downwardly thereinto through the opening at the upper end of the support tube with the mount thereof engaging the upper end of the support tube to limit the downward movement of the needle into the support tube. In one embodiment of the invention, the upper side of the base member has at least one opening formed therein for supporting a syringe therein in a vertically disposed sterile condition.

In the preferred embodiment, a receptacle extends upwardly from the base member which is configured to have an injection needle assembly selectively removably positioned therein.

Although the drawings illustrate a plurality of support tubes, a single support tube could extend upwardly from the base member.

It is therefore a principal object of the invention to provide an improved sterile stand for supporting surgical instruments or medical tools thereon.

A further object of the invention is to provide a sterile stand for supporting epidural needles, cannulas, syringes thereon and for supporting an injection needle assembly thereon.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

FIG. 7A is a side view of the second embodiment of the stand with the cannulas, syringes and injection needle assembly being positioned on the stand; and FIG. 7B is a sectional view of the embodiment of the stand as seen on lines 7A and 7B of FIG. 7A.

DESCRIPTION OF THE PREFERRED EMBODIMENT

Figure 1:
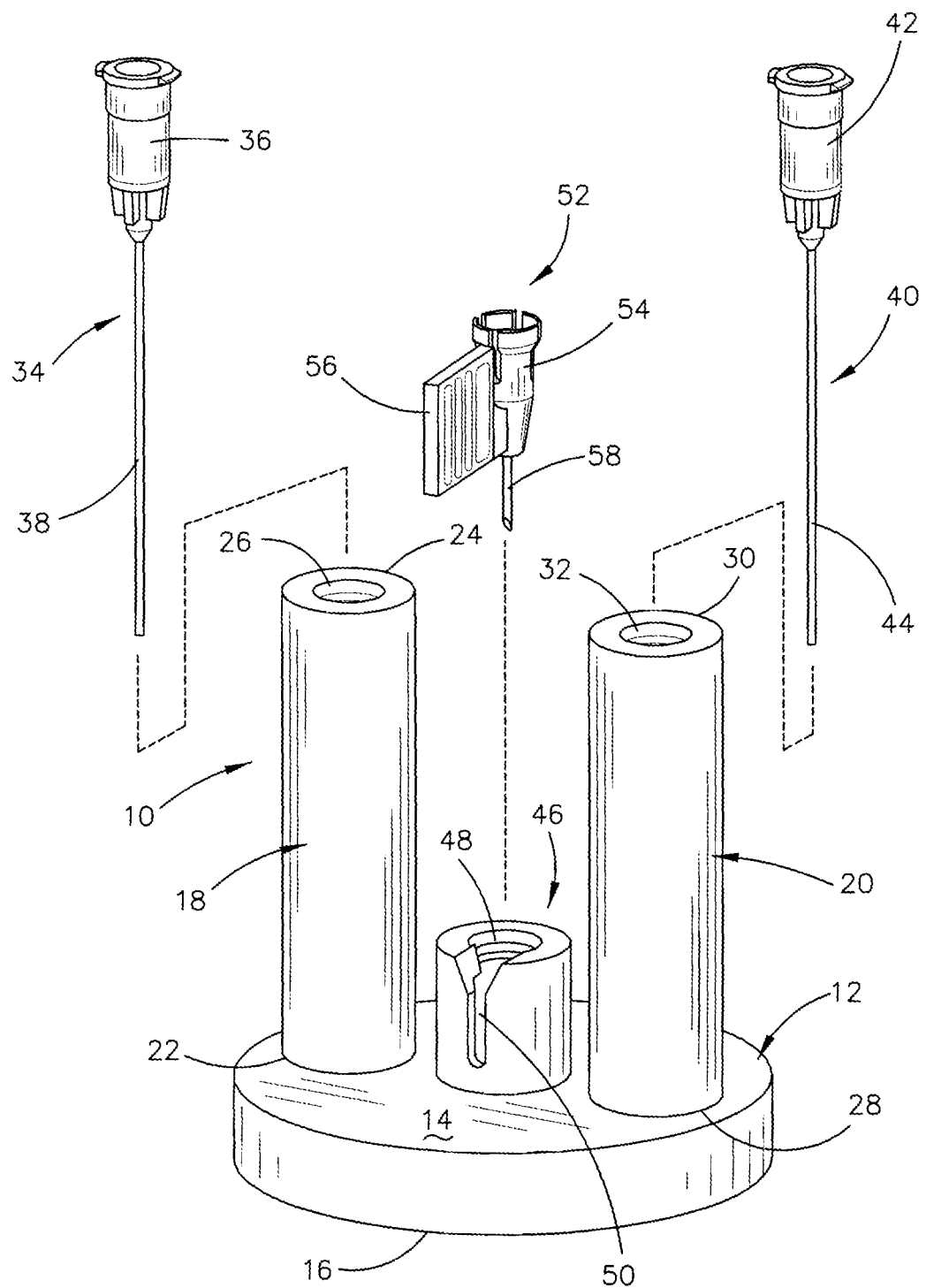
FIG. 1 is an exploded perspective view of one embodiment of the stand of this invention and which illustrates a pair of cannulas and an injection needle assembly which may be positioned on or in the stand.

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

The first embodiment of the stand of this invention is referred to generally by the reference numeral 10. Stand 10 includes a horizontally disposed base member 12 having an upper side 14 and a lower side 16. In the first embodiment of the invention, a pair of vertically disposed hollow sterile support tubes 18 and 20 are secured to and extend upwardly from the base member 12 in a horizontally spaced-apart manner. It should be noted that a single support tube could be used or a plurality of support tubes could be used as will be explained hereinafter.

Support tube 18 will be described as having a lower end 22 and an upper end 24. The upper end 24 of support tube 18 is closed except for an opening or bore 26 formed therein which extends downwardly thereinto. The opening or bore 26 has a diameter which is less than the diameter of support tube 18. Support tube 20 will be described as having a lower end 28 and an upper end 30. The upper end 30 of support tube 20 is closed except for an opening or bore 32 formed therein which extends downwardly thereinto. The opening or bore 26 has a diameter which is less than the diameter of support tube 20. The lower ends of openings or bores 26 and 32 are closed to maintain a sterile barrier at the lower ends thereof.

The numeral 34 refers to a blunt tip cannula which includes a mount 36 and a needle portion 38 extending therefrom. The numeral 40 refers to a blunt tip cannula which includes a mount 42 and a needle portion 44. The needle portion 38 of cannula 34 is selectively removably inserted downwardly through opening or bore 26 in support tube 18 until the mount 36 engages the upper end 24 of support tube 18. Cannula 40 is similarly inserted into support tube 20.

Although the drawings illustrate blunt tip cannulas 34 and 40, epidural needles such as disclosed in U.S. patent application Ser. No. 15/354,249 could be substituted for the cannulas 34 and 40. The primary difference between the cannulas 34 and 40 and the epidural needles of U.S. Pat. No. 15,354,249 is that the tips of the needle portions 38 and 44 of cannulas 34 and 40 are blunt while the tips of the epidural needles are sharpened.

Figure 2:
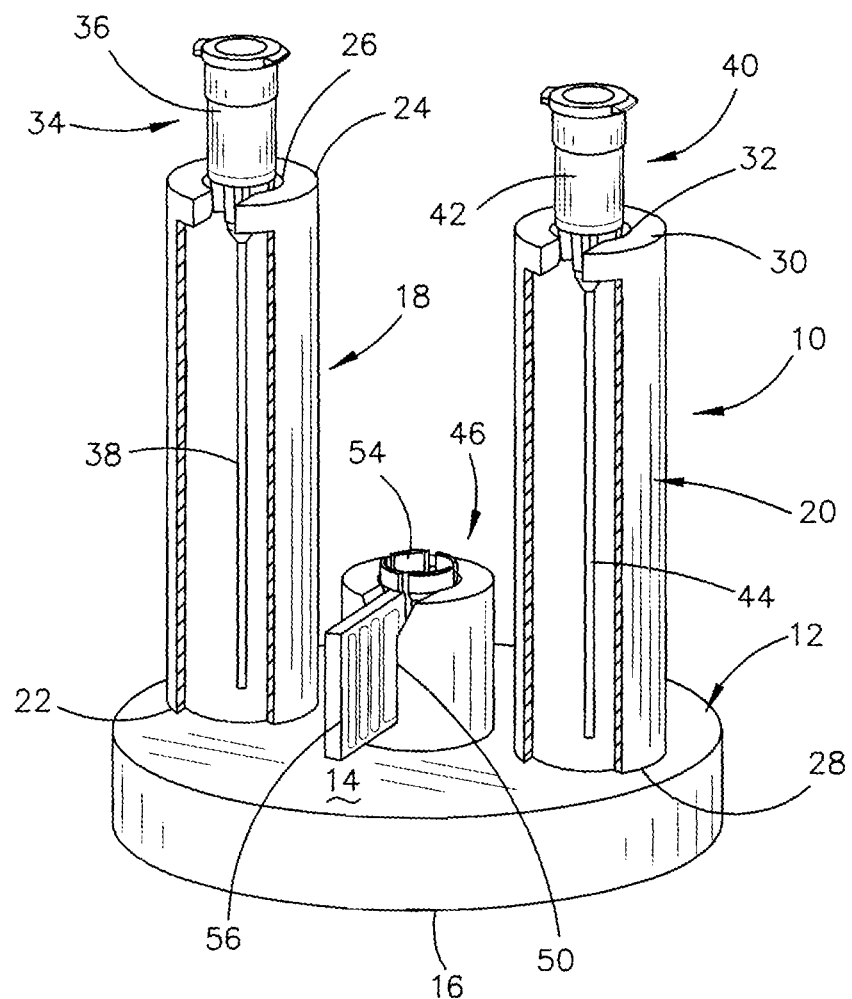
FIG. 2 is a perspective view of the stand of FIG. 1 with the cannulas and injection needle assembly positioned thereon with a portion of the support tubes cut-away to more fully illustrate the invention.
Figure 3:
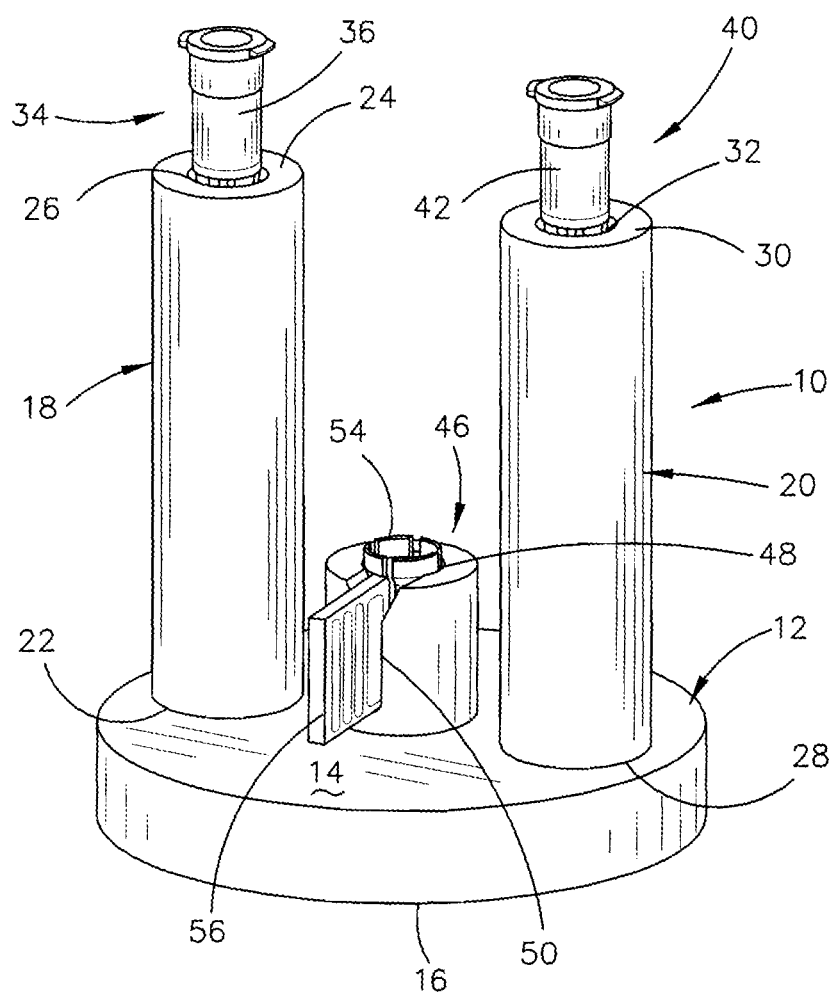
FIG. 3 is a view similar to FIG. 2 except that the support tubes have not been cut-away as seen in FIG. 2.

The stand 10 of FIGS. 1-3 also includes an optional tubular receptacle 46 which extends upwardly from base member 12 as seen in the drawings. Receptacle 46 includes a central bore 48 which extends downwardly thereinto. Bore 48 extends downwardly into base member 12. The lower end of bore 48 is closed to maintain a sterile barrier at the lower end thereof. Receptacle 46 also includes a slot 50 formed in one side thereof which communicates with bore 48. The receptacle 46 is configured to have a sterile injection needle assembly 52 selectively positioned therein and thereon as seen in the drawings. Assembly 52 includes a mount 54, wing 56 and needle 58. The wing 56 of assembly 52 extends outwardly through slot 50.

Thus, when the epidural needle or cannula needs to be removed from the patient, the epidural needle or cannula, after being removed from the patient, is inserted downwardly into the associated support tube which ensures that the needle or cannula will remain in a sterile condition if it or they are going to be used again.

Figure 4:
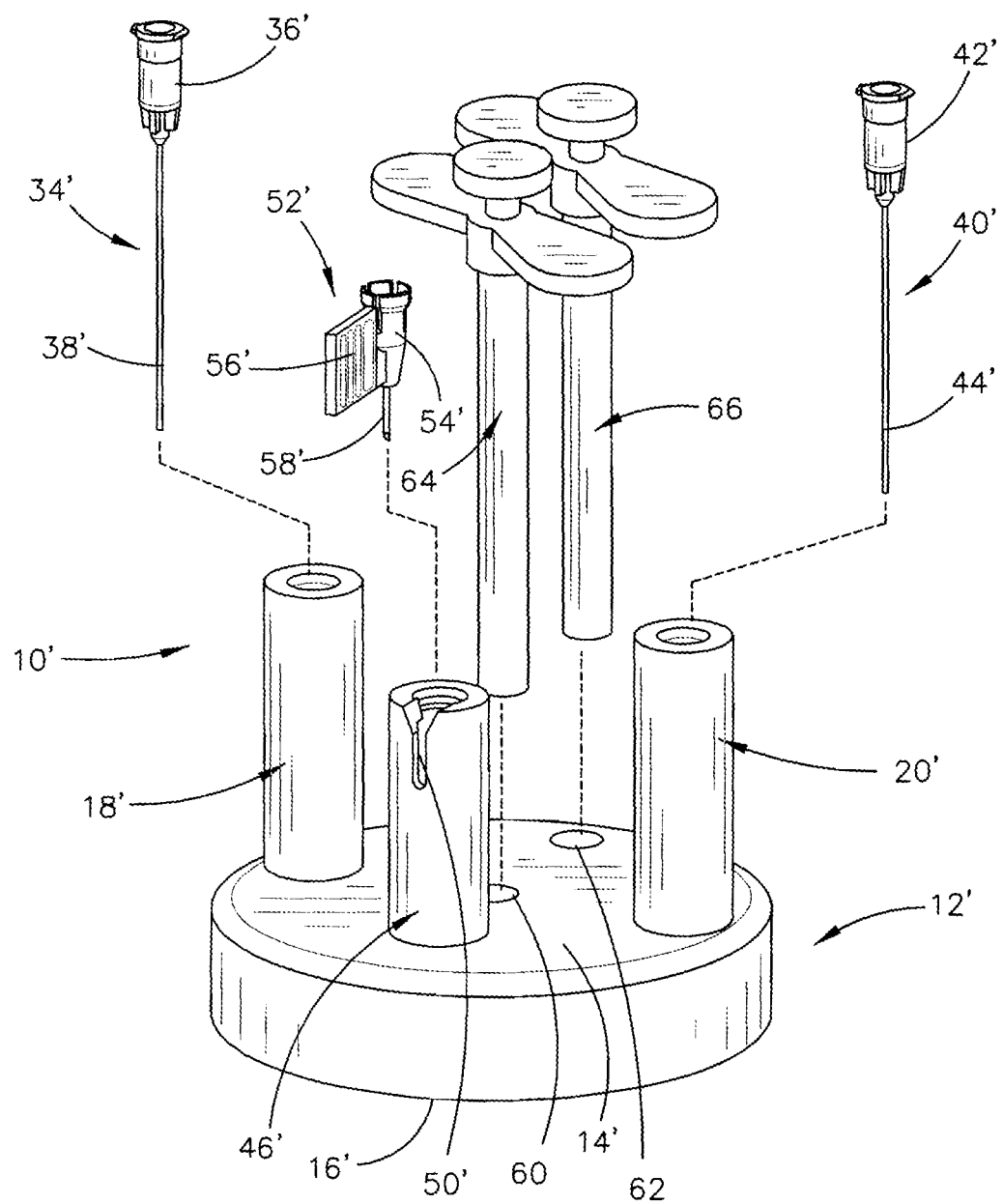
FIG. 4 is an exploded perspective view of a second embodiment of the stand of the invention which illustrates the stand being capable of supporting a pair of syringes thereon.
Figure 5:
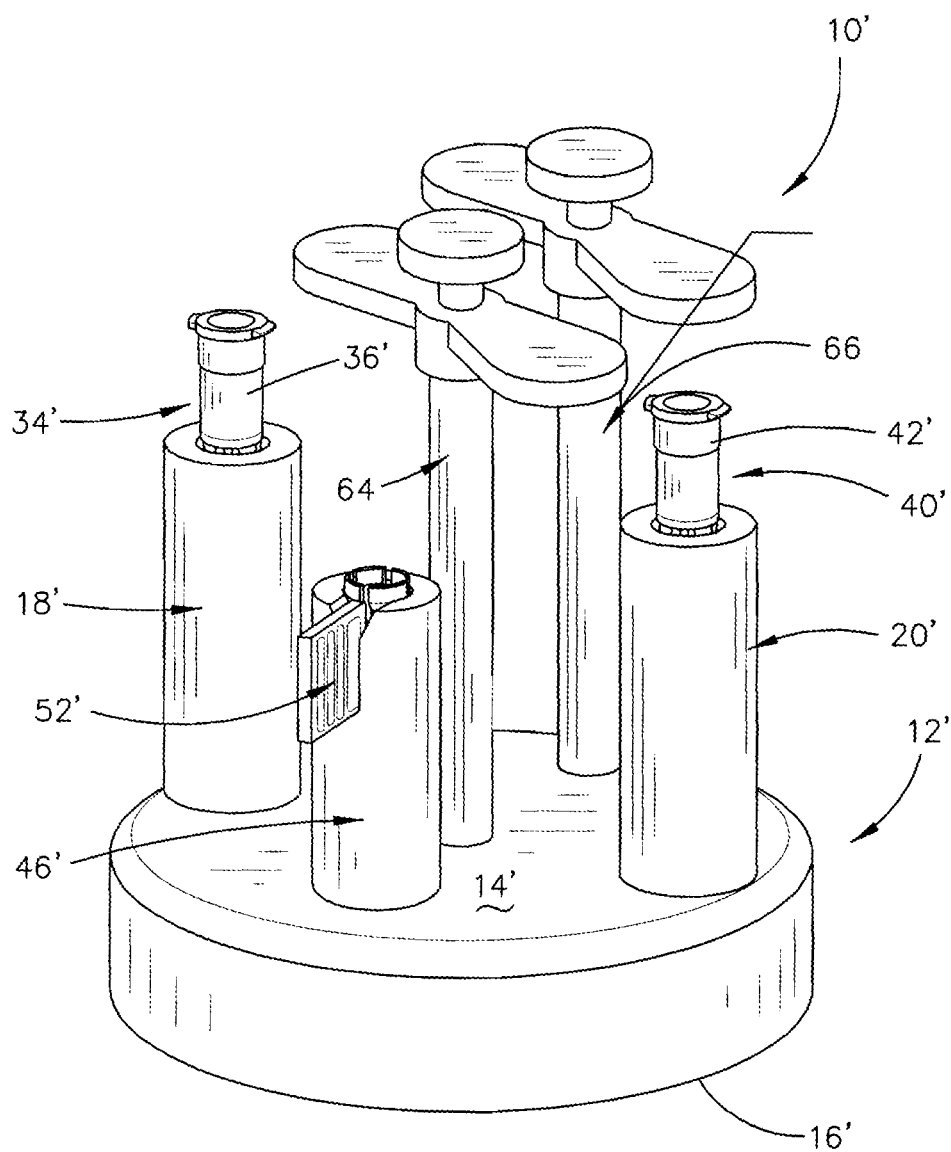
FIG. 5 is a perspective view of the stand of FIG. 4 with the cannulas, syringes and injection needle assembly being positioned on the stand.

The second embodiment of the stand of the invention is illustrated in FIGS. 4 and 5 and is identified by the reference numeral 10'. Stand 10' is similar to stand 10 with "'" being used to designate structure on stand 10' which is the same as the structure of stand 10.

Stand 10' is identical to stand 10 except that a pair of openings 60 and 62 are formed in the upper side 14' of base member 12' which are adapted to selectively receive the lower ends of syringes 64 and 66 respectively. The lower ends of the openings 60 and 62 terminate above the lower side 16' of base member 12' to maintain a sterile barrier at the lower ends thereof so that the syringes 64 and 66 are maintained in a sterile condition.

Figure 6:
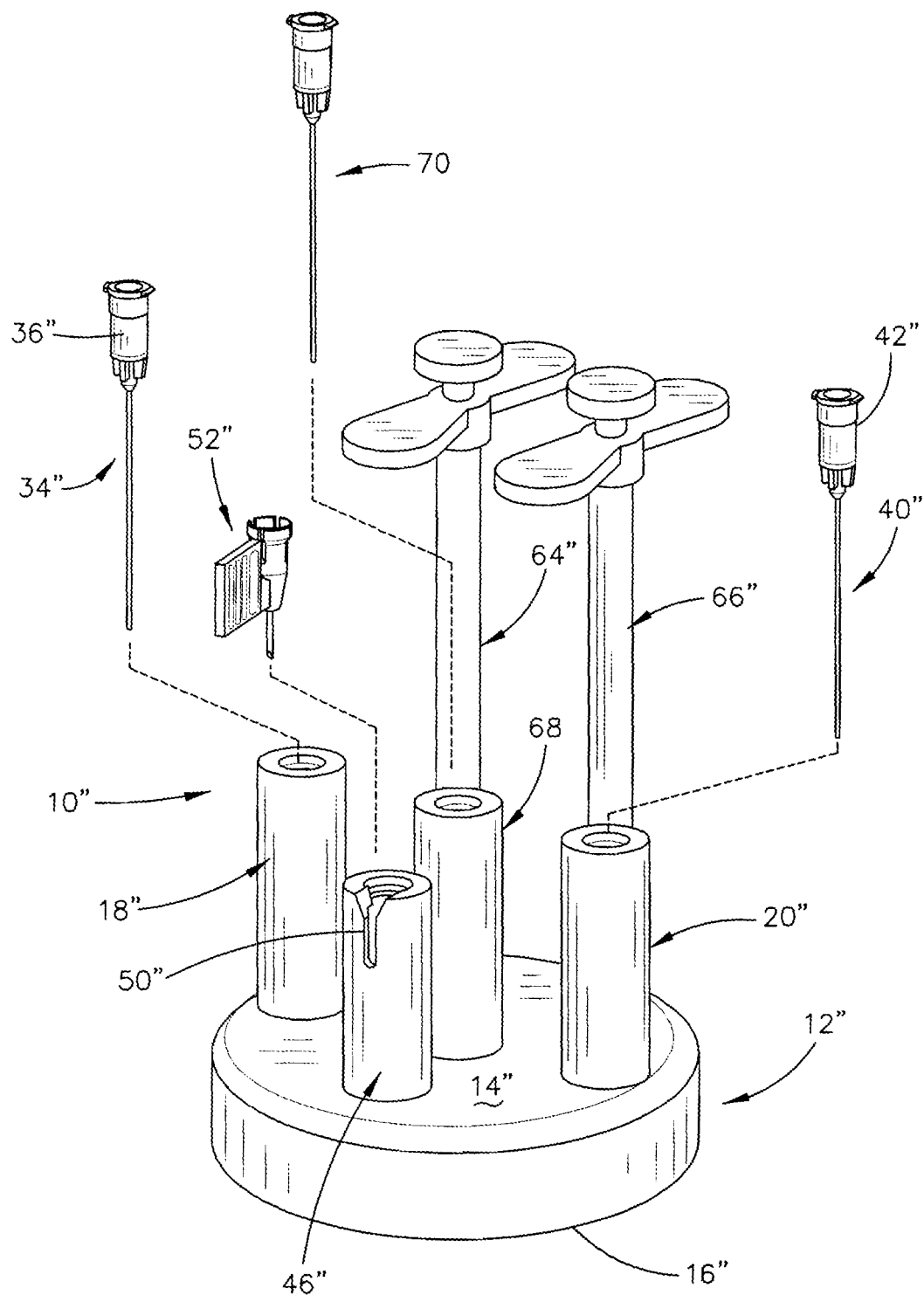
FIG. 6 is an exploded perspective view of a third embodiment of the stand of this invention and which is similar to the embodiment of FIG. 4 except that the stand includes a third support tube for supporting a third cannula thereon.

The third embodiment of the stand of the invention is illustrated in FIG. 6 and is designated by the reference numeral 10". Stand 10" is identical to 10' with "''" being used on FIG. 6 to designate structure on stand 10'. The only difference between stands 10' and 10" is that stand 10" includes a third support tube 68 which extends upwardly from base member 12" and which is configured to receive and support a third cannula 70 thereon.

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

We claim:

1. In combination:

an elongated surgical needle, having a lower end and an upper end, with said surgical needle having an enlarged mount at said upper end thereof;

a stand for supporting said surgical needle in a vertically disposed sterile manner;

said stand comprising:

(a) a horizontally disposed base member having a flat lower side and a flat upper side;

(b) a vertically disposed and elongated hollow sterile support tube having a lower end and an upper end;

(c) said lower end of said support tube being secured to said flat upper side of said base member so as to extend upwardly from said flat upper side of said base member;

(d) said support tube having a bore, with upper and lower ends, formed therein which extends downwardly into said upper end of said support tube; and (e) said support tube configured to have said elongated surgical needle extending downwardly thereinto through said bore of said support tube with said enlarged mount engaging said upper end of said support tube to limit the downward movement of said surgical needle into said support tube with said support tube having a length which is sufficient whereby the entire length of said surgical needle, below said enlarged mount, is positioned in said bore of said support tube above said flat upper side of said base member.

2. The combination of claim 1 wherein a tubular receptacle extends upwardly from said base member which is configured to have an injection needle assembly selectively removably positioned therein above said flat upper side of said base member.

3. The combination of claim 1 wherein a plurality of vertically disposed and elongated hollow sterile support tubes, which are identical to one another, are secured to said flat upper side of said base member and extend upwardly therefrom in a horizontally spaced-apart manner so as not to communicate with one another with each of said support tubes being configured to support a surgical needle therein in a sterile manner.

4. The combination of claim 1 wherein at least one syringe is selectively secured to said base member so as to extend upwardly therefrom.

5. The combination of claim 1 wherein said base member is circular.

\* \* \* \* \*